United States Patent
Sugita et al.

(10) Patent No.: US 7,037,994 B2
(45) Date of Patent: May 2, 2006

(54) ACENAPHTHYLENE DERIVATIVE, POLYMER, AND ANTIREFLECTION FILM-FORMING COMPOSITION

(75) Inventors: Hikaru Sugita, Yokkaichi (JP); Keiji Konno, Yokkaichi (JP); Masato Tanaka, Yokkaichi (JP); Tsutomu Shimokawa, Suzuka (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 10/624,678

(22) Filed: Jul. 23, 2003

(65) Prior Publication Data

US 2004/0034155 A1 Feb. 19, 2004

(30) Foreign Application Priority Data

Jul. 31, 2002 (JP) ............................. 2002-224138
Nov. 8, 2002 (JP) ............................. 2002-324709

(51) Int. Cl.
- C08F 32/08 (2006.01)
- C08F 12/32 (2006.01)
- C08F 132/08 (2006.01)

(52) U.S. Cl. ............... 526/284; 526/280; 526/346.1; 526/346; 526/332; 528/396

(58) Field of Classification Search ............... 528/396; 526/280, 284, 346, 346.1, 332
See application file for complete search history.

(56) References Cited

U.S. PATENT DOCUMENTS

| | | | | |
|---|---|---|---|---|
| 4,093,678 A | * | 6/1978 | Bailey et al. | 525/210 |
| 4,373,046 A | * | 2/1983 | Hagiwara et al. | 524/285 |
| 4,569,963 A | * | 2/1986 | Hisaki et al. | 524/458 |
| 4,604,438 A | * | 8/1986 | Beuhler et al. | 526/262 |
| 5,629,393 A | * | 5/1997 | Varshney et al. | 526/175 |
| 5,654,121 A | * | 8/1997 | Eichhorn et al. | 430/157 |
| 5,866,659 A | * | 2/1999 | Chung et al. | 525/279 |
| 2002/0086934 A1 | * | 7/2002 | Kawaguchi et al. | 524/544 |
| 2003/0073040 A1 | | 4/2003 | Iwasawa et al. | |

FOREIGN PATENT DOCUMENTS

| EP | 1 205 805 | | 5/2002 |
|---|---|---|---|
| EP | 1 205 805 A1 | * | 5/2002 |
| JP | 56-122862 | * | 9/1981 |
| JP | 57-135818 | * | 8/1982 |
| JP | 58-38711 | * | 3/1983 |
| JP | 59-093448 | | 5/1984 |
| JP | 61-285233 | * | 12/1986 |
| JP | 3-100005 | * | 4/1991 |
| JP | 6-161111 | * | 6/1994 |
| JP | 06-161111 | | 6/1994 |
| JP | 8-184966 A | * | 7/1996 |
| JP | 9-230596 A | * | 9/1997 |
| JP | 10-90885 A | * | 4/1998 |
| JP | 2000-143937 | | 5/2000 |
| JP | 2001-40293 | | 2/2001 |
| JP | 2002-3543 | * | 1/2002 |
| WO | WO 01/13179 A1 | * | 2/2001 |

OTHER PUBLICATIONS

JP 9-230596 (abstract and translation in English).*
JP 8-184966 (abstract and translation in English).*
JP 10-90885 (abstract and translation in English).*
Carpino, L.A.; Goewecke, S. J. Org. Chem. 1964, 29, 2824-30 (abstract only).*
McMurry, "Organic Chemistry", Brooks/Cole Publishing Company, Monterey, California, p. 690, (1984).

* cited by examiner

Primary Examiner—David W. Wu
Assistant Examiner—Rip A. Lee
(74) Attorney, Agent, or Firm—Merchant & Gould

(57) ABSTRACT

Novel compounds acetoxymethylacenaphthylene and hydroxymethylacenaphthyleneare disclosed. A polymer prepared from these novel compounds containing a structural unit of the formula (3),

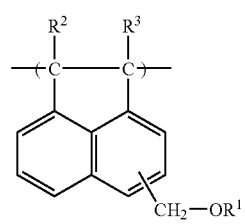

(3)

wherein $R^1$ is a hydrogen atom and $R^2$ and $R^3$ individually represent a monovalent atom or a monovalent organic group is also disclosed. The polymer is suitable as a component for an antireflection film-forming composition exhibiting a high antireflection effect and not causing intermixing with a resist film.

15 Claims, No Drawings und ACENAPHTHYLENE DERIVATIVE, POLYMER, AND ANTIREFLECTION FILM-FORMING COMPOSITION

BACKGROUND OF THE INVENTION

1. Field of the Invention

The present invention relates to acetoxymethylacenaphthylene, hydroxymethylacenaphthylene, a polymer prepared from the acetoxymethylacenaphthylene or hydroxymethylacenaphthylene, and an antireflection film-forming composition comprising the polymer suitable for use in microfabrication using a lithography process which utilizes various radiations, particularly for manufacturing highly integrated circuit elements.

2. Description of Background Art

Production of polyacenaphthylene by polymerizing acenaphthylene and production of copolymers by copolymerizing acenaphthylene with styrene, maleic anhydride, or the like are well known in the art.

Such acenaphthylene polymers and copolymers (hereinafter collectively referred to as (co)polymers) are highly reactive due to their unique structure. Chemical reactions of such (co)polymers with various reactive reagents have been investigated and details of their properties such as luminous actions have been reported. Various materials possessing properties such as low hygroscopicity, low birefringence, and low dielectric constant, as well as utilization of such materials have been developed.

Providing acenaphthylene derivatives possessing various functional groups useful as raw materials for manufacturing acenaphthylene (co) polymers is very important from academic and industrial viewpoints in developing the acenaphthylene (co)polymers that are highly reactive and expected to have various characteristics. Various acenaphthylene derivatives having an aromatic ring substituted with a hydroxyl group, alkyl group, halomethyl group, halogen, or the like have already been synthesized.

However, no acenaphthylene derivatives having an aromatic ring substituted with an acetoxymethyl group or hydroxymethyl group have been reported heretofore.

The fabrication size in a lithography process for manufacturing integrated circuit elements is becoming smaller to achieve a higher degree of integration. In the lithography process, a resist composition solution is applied to a substrate, a mask pattern is transcribed on the resist by a stepper (reducing projection aligner), and the resist is developed using a suitable developer to obtain a desired pattern. However, the substrate having a high reflectance such as aluminum, aluminum-silicon alloy, aluminum-silicon-copper alloy, polysilicon, or tungsten silicide used in this process reflects radiation on the surface and produces halation on a resist pattern, making it impossible to precisely reproduce a fine resist pattern.

To overcome this problem, a method of providing an antireflection film that can absorb radiation reflected on the surface of the substrate under the resist film to be formed on the substrate has been proposed. Inorganic films such as a titanium film, titania film, titanium nitride film, chromium oxide film, carbon film, and α-silicon film formed by vacuum deposition, CVD, sputtering, or the like are known as such an antireflection film. These inorganic antireflection films, however, have drawbacks such as conductivity which precludes these films from being used for production of integrated circuits and requirement of a special apparatus for forming such as a vacuum deposition apparatus, CVD apparatus, and sputtering apparatus.

As a material overcoming these drawbacks of inorganic antireflection films, an organic antireflection film made from a polyamide acid (co)polymer or polysulfone (co)polymer and a dye has been proposed (see Japanese Patent Application Laid-open No. 59-93448, for example). This organic antireflection film has no conductivity. In addition, since the composition from which the film is formed is dissolvable in common solvents, the composition can be applied to a substrate as easily as a resist composition solution without requiring a special apparatus.

However, since the organic antireflection film made from a polyamide acid (co)polymer or polysulfone (co)polymer and a dye limits the amount of the dye that can be added, the film cannot sufficiently prevent halation and standing waves. In addition, because such an organic film migrates with a resist film in a slight amount (a phenomenon known as intermixing), a resist pattern may have an impaired sectional configuration (an impaired pattern profile) such as inadequate dyeing and a skirt shape.

On the other hand, a polymer having an acenaphthylene skeleton is known to overcome the above-described problems to a considerable extent, if applied to an antireflection film (see Japanese Patent Applications Laid-open No. 2000-143937 and No. 2001-402933, for example). The antireflection film, however, cannot necessarily overcome the problem of intermixing.

As a means for overcoming this problem, a method of crosslinking the polymer having an acenaphthylene skeleton with formaldehyde or the like is thought to be effective. This method, however, may impair storage stability of the antireflection film-forming composition stored in the form of a solution.

Development of an improved antireflection film that can overcome the problems in conventional technologies and development of a polymer useful as a polymer component for such an antireflection film have therefore been desired.

The subject of the present invention is to overcome the above-described problems in conventional technologies and provide an antireflection film-forming composition exhibiting high antireflection effect and capable of forming resist patterns excelling in resolution, pattern configuration, and the like, without intermixing, to provide a polymer useful particularly as a component for the antireflection film-forming composition, and to provide acenaphthylene derivatives useful particularly as a raw material or an intermediate for the polymer.

As a result of extensive studies to solve the above problems, the inventors of the present invention have found that a novel acenaphthylene derivative easily synthesized from a readily available acenaphthene by a process involving well-known organic synthesis reactions is very useful as a raw material or an intermediate for a polymer that can effectively solve the above problems relating to antireflection films. The inventors have further found that a novel polymer having an aromatic ring with a specific substituent that can be produced from the acenaphthylene derivative exhibits a high absorbance of an excimer laser or other radiations and a high refractive index in comparison with conventional antireflection films, and that excellent antireflection films can be produced by using the polymer as an antireflection film-forming composition. The findings have led to the completion of the present invention.

SUMMARY OF THE INVENTION

An object of the present invention is to provide acetoxymethylacenaphthylene of the following formula (1).

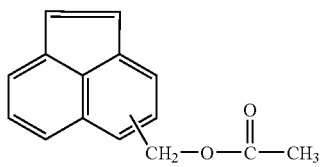
(1)

Another object of the present invention is to provide hydroxymethylacenaphthylene of the following formula (2).

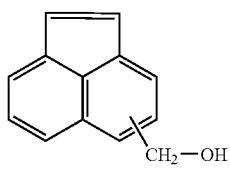
(2)

A still another object of the present invention is to provide a polymer (hereinafter referred to as "polymer (I)") having a structural unit of the following formula (3) (hereinafter referred to as "structural unit (3)") and having a polystyrene-reduced weight average molecular weight determined by gel permeation chromatography (GPC) in the range of 500–10,000,

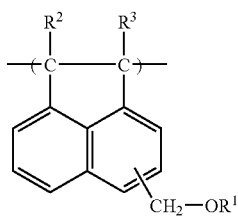
(3)

wherein $R^1$ represents a hydrogen atom or a monovalent organic group and $R^2$ and $R^3$ individually represent a monovalent atom or a monovalent organic group.

Yet another object of the present invention is to provide an antireflection film-forming composition comprising the polymer (I) and a solvent.

A further object of the present invention is to provide an antireflection film-forming composition comprising a polymer (hereinafter referred to as "polymer (II)") having a structural unit of the following formula (4) (hereinafter referred to as "structural unit (4)") and a solvent,

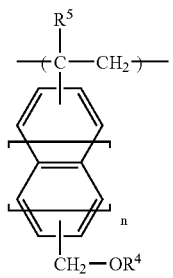
(4)

wherein $R^4$ is a hydrogen atom or a monovalent organic group, $R^5$ is a monovalent atom or a monovalent organic group, and n is 0 or 1.

A still further object of the present invention is to provide an antireflection film-forming composition comprising at least one polymer selected from the group consisting of a polymer (hereinafter referred to as "polymer (III)") having the structural unit (3) and the structural unit (4), a polymer (hereinafter referred to as "polymer (IV)") having the structural unit (3) and a structural unit of the following formula (5) (hereinafter referred to as "structural unit (5)"), and a polymer (hereinafter referred to as "polymer (V)") having the structural unit (4) and the structural unit (5) and a solvent,

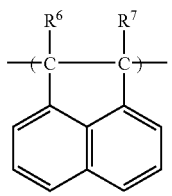
(5)

wherein $R^6$ and $R^7$ individually represent a monovalent atom or a monovalent organic group.

DETAILED DESCRIPTION OF THE INVENTION AND PREFERRED EMBODIMENTS

The present invention is described below in detail.

Acetoxymethylacenaphthylene and hydroxymethylacenaphthylene

The acetoxymethyl group in the formula (1) or hydroxylmethyl group in the formula (2) bonds to either one of the 3 to 5 positions of the acenaphthylene.

The acetoxymethylacenaphthylene of the formula (1) (hereinafter referred to as "acetoxymethylacenaphthylene (1)") can be synthesized by a process comprising the following steps 1–4. The hydroxymethylacenaphthylene of the formula (2) (hereinafter referred to as "hydroxymethylacenaphthylene (2)") can be synthesized by the following step 5.

Step 1: Acenaphthene is formylated by a conventional method as shown in the following formula (i).

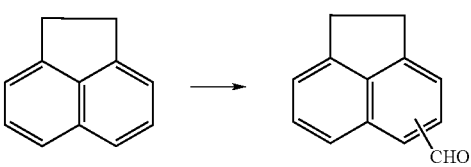
(i)

Step 2: The formyl group in the formyl acenaphthene obtained in Step 1 is reduced by a conventional method to obtain hydroxymethylacenaphthene as shown in the following formula (ii).

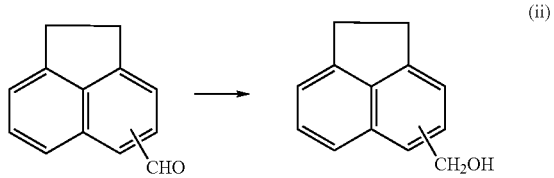

(ii)

Step 3: The hydroxyl group in the hydroxymethylacenaphthene obtained in Step 2 is acetylated by a conventional method to obtain acetoxymethylacenaphthene as shown in the following formula (iii).

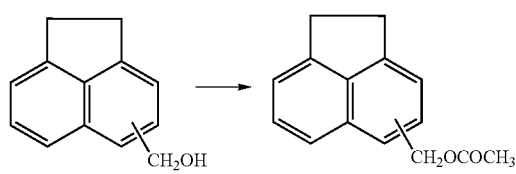

(iii)

Step 4: The acetoxymethylacenaphthene obtained in Step 3 is dehydrogenated by a conventional method to obtain acetoxymethylacenaphthylene (1) as shown in the following formula (iv).

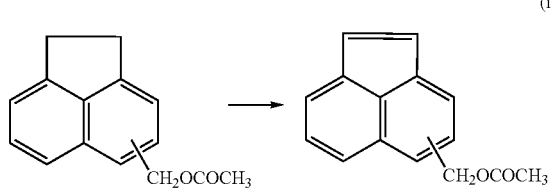

(iv)

Step 5: The acetoxy group in the acetoxymethylacenaphthylene obtained in Step 4 is hydrolyzed by a conventional method to obtain hydroxymethylacenaphthylene (2) as shown in the following formula (v).

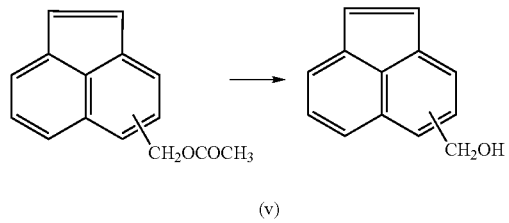

(v)

Acetoxymethylacenaphthylene (1) can be suitably used not only as a raw material or an intermediate material for manufacturing the polymer (I), polymer (III), and polymer (IV), but also as a raw material for synthesizing hydroxymethylacenaphthylene (2).

Acetoxymethylacenaphthylene (1) is also used as a raw material or an intermediate for synthesizing other related acenaphthylene derivatives.

Hydroxymethylacenaphthylene (2) can be suitably used not only as a raw material or an intermediate material for manufacturing the polymer (I), polymer (III), and polymer (IV), but also as a raw material for synthesizing acetoxymethylacenaphthylene (1).

Hydroxymethylacenaphthylene (2) is also used as a raw material or an intermediate for synthesizing other related acenaphthylene derivatives.

Polymer (I)

As the monovalent organic group represented by $R^1$ in the structural unit (3), groups having 1–10 carbon atoms are preferable. Examples of the preferable organic group are a phenyl group, alkyl group, alkenyl group, acyl group, and groups in which one or more hydrogen atoms on the phenyl group, alkyl group, or alkenyl group are replaced by one or more, the same or different, substituents such as a halogen atom, hydroxyl group, mercapto group, carboxyl group, nitro group, and sulfonic acid group.

As the alkyl group, linear or branched alkyl groups having 1–6 carbon atoms are preferable. A methyl group, ethyl group, n-propyl group, i-propyl group, n-butyl group, i-butyl group, sec-butyl group, and t-butyl group, for example, are particularly preferable.

As the alkenyl group, linear or branched alkenyl groups having 2–6 carbon atoms are preferable. Particularly preferable examples are a vinyl group, allyl group, methallyl group, 1-butenyl group, and 2-butenyl group.

As the acyl group, aliphatic or aromatic acyl groups having 2–6 carbon atoms are preferable. Particularly preferable examples are an acetyl group, propionyl group, butyryl group, and benzoyl group.

As examples of the monovalent atom represented by $R^2$ or $R^3$ in the structural unit (3), a hydrogen atom and a halogen atom such as a fluorine atom, chlorine atom, or bromine atom can be given.

As examples of the monovalent organic group represented by $R^2$ or $R^3$, the same groups as those previously given for the monovalent organic group represented by $R^1$ can be given.

Particularly preferable groups for $R^1$ in the structural unit (3) are a hydrogen atom, methyl group, acetyl group, and the like.

Preferable groups for $R^2$ or $R^3$ are a hydrogen atom, methyl group, phenyl group, and the like.

The polymer (I) can be prepared by polymerizing an acenaphthylene corresponding to the structural unit (3), optionally together with a copolymerizable unsaturated monomer by radical polymerization, anionic polymerization, cationic polymerization, or the like using an appropriate process such as a mass polymerization process or solution polymerization process.

The polymer (I) having the structural unit (3) in which the $R^1$ group is a hydrogen atom can be produced by hydrolyzing the acetoxy group of the polymer (I) having the structural unit (3) in which the $R^1$ group is an acetyl group by a conventional method. The polymer (I) having the structural unit (3) in which the $R^1$ group is an acetyl group can be produced by acetylating the hydroxyl group of the polymer (I) having the structural unit (3) in which the $R^1$ group is a hydrogen atom by a conventional method.

The following compounds can be given as examples of the acenaphthylene corresponding to the structural unit (3): hydroxymethylacenaphthylenes such as
3-hydroxymethylacenaphthylene,
4-hydroxymethylacenaphthylene,
5-hydroxymethylacenaphthylene, 1-methyl-3-hydroxymethylacenaphthylene,
1-methyl-4-hydroxymethylacenaphthylene,
1-methyl-5-hydroxymethylacenaphthylene,
1-methyl-6-hydroxymethylacenaphthylene,
1-methyl-7-hydroxymethylacenaphthylene,
1-methyl-8-hydroxymethylacenaphthylene,
1,2-dimethyl-3-hydroxymethylacenaphthylene,
1,2-dimethyl-4-hydroxymethylacenaphthylene,
1,2-dimethyl-5-hydroxymethylacenaphthylene,
1-phenyl-3-hydroxymethylacenaphthylene,
1-phenyl-4-hydroxymethylacenaphthylene,
1-phenyl-5-hydroxymethylacenaphthylene,
1-phenyl-6-hydroxymethylacenaphthylene,
1-phenyl-7-hydroxymethylacenaphthylene,
1-phenyl-8-hydroxymethylacenaphthylene,
1,2-diphenyl-3-hydroxymethylacenaphthylene,
1,2-diphenyl-4-hydroxymethylacenaphthylene, and
1,2-diphenyl-5-hydroxymethylacenaphthylene;
acetoxymethylacenaphthylenes such as
3-acetoxymethylacenaphthylene,
4-acetoxymethylacenaphthylene,
5-acetoxymethylacenaphthylene,
1-methyl-3-acetoxymethylacenaphthylene,
1-methyl-4-acetoxymethylacenaphthylene,
1-methyl-5-acetoxymethylacenaphthylene,
1-methyl-6-acetoxymethylacenaphthylene,
1-methyl-7-acetoxymethylacenaphthylene,
1-methyl-8-acetoxymethylacenaphthylene,
1,2-dimethyl-3-acetoxymethylacenaphthylene,
1,2-dimethyl-4-acetoxymethylacenaphthylene,
1,2-dimethyl-5-acetoxymethylacenaphthylene,
1-phenyl-3-acetoxymethylacenaphthylene,
1-phenyl-4-acetoxymethylacenaphthylene,
1-phenyl-5-acetoxymethylacenaphthylene,
1-phenyl-6-acetoxymethylacenaphthylene,
1-phenyl-7-acetoxymethylacenaphthylene,
1-phenyl-8-acetoxymethylacenaphthylene,
1,2-diphenyl-3-acetoxymethylacenaphthylene,
1,2-diphenyl-4-acetoxymethylacenaphthylene, and
1,2-diphenyl-5-acetoxymethylacenaphthylene;
methoxymethylacenaphthylenes such as
3-methoxymethylacenaphthylene,
4-methoxymethylacenaphthylene,
5-methoxymethylacenaphthylene,
1-methyl-3-methoxymethylacenaphthylene,
1-methyl-4-methoxymethylacenaphthylene,
1-methyl-5-methoxymethylacenaphthylene,
1-methyl-6-methoxymethylacenaphthylene,
1-methyl-7-methoxymethylacenaphthylene,
1-methyl-8-methoxymethylacenaphthylene,
1,2-dimethyl-3-methoxymethylacenaphthylene,
1,2-dimethyl-4-methoxymethylacenaphthylene,
1,2-dimethyl-5-methoxymethylacenaphthylene,
1-phenyl-3-methoxymethylacenaphthylene,
1-phenyl-4-methoxymethylacenaphthylene,
1-phenyl-5-methoxymethylacenaphthylene,
1-phenyl-6-methoxymethylacenaphthylene,
1-phenyl-7-methoxymethylacenaphthylene,
1-phenyl-8-methoxymethylacenaphthylene,
1,2-diphenyl-3-methoxymethylacenaphthylene,
1,2-diphenyl-4-methoxymethylacenaphthylene, and
1,2-diphenyl-5-methoxymethylacenaphthylene;
3-phenoxymethylacenaphthylene,
4-phenoxymethylacenaphthylene,
5-phenoxymethylacenaphthylene,
3-vinyloxymethylacenaphthylene,
4-vinyloxymethylacenaphthylene, and
5-vinyloxymethylacenaphthylene.

Of these acenaphthylenes,
3-hydroxymethylacenaphthylene,
4-hydroxymethylacenaphthylene,
5-hydroxymethylacenaphthylene,
3-acetoxymethylacenaphthylene,
4-acetoxymethylacenaphthylene,
5-acetoxymethylacenaphthylene,
3-methoxymethylacenaphthylene,
4-methoxymethylacenaphthylene, and
5-methoxymethylacenaphthylene are particularly preferable.

These acenaphthylenes may be used either individually or in combinations of two or more.

As other copolymerizable unsaturated compounds used for the polymer (I), aromatic vinyl compounds corresponding to the later described structural unit (4) and acenaphthenes corresponding to the later described structural unit (5) are preferable.

The following compounds can be given as examples of the other copolymerizable unsaturated compounds: aromatic vinyl compounds such as styrene, α-methylstyrene, 2-methylstyrene, 3-methylstyrene, 4-methylstyrene, 1-vinylnaphthalene, 2-vinylnaphthalene, 9-vinylanthracene, and 9-vinylcarbazole; vinyl esters such as vinyl acetate, vinyl propionate, and vinyl caprate; cyanated vinyl compounds such as (meth)acrylonitrile, α-chloroacrylonitrile, and cyanated vinylidene; unsaturated carboxylic acid esters such as methyl (meth)acrylate, ethyl (meth)acrylate, n-propyl (meth)acrylate, isopropyl (meth)acrylate, n-butyl (meth)acrylate, t-butyl (meth)acrylate, n-hexyl (meth)acrylate, and glycidyl (meth)acrylate; unsaturated group-containing unsaturated carboxylates such as ethylene glycol di(meth)acrylate, propylene glycol di(meth)acrylate, vinyl (meth)acrylate, and dimethyl.vinyl.(meth)acryloyloxymethylsilane; halogen-containing vinyl compounds such as 2-chloroethyl vinyl ether, vinyl chloroacetate, and allyl chloroacetate; hydroxyl group-containing vinyl compounds such as 2-hydroxyethyl (meth)acrylate, 2-hydroxypropyl (meth)acrylate, and (meth)allyl alcohol; amide group-containing vinyl compounds such as (meth) acryl amide and crotonic acid amide; and carboxyl group-containing vinyl compounds such as mono-[2-(meth)acryloyloxyethyl] succinate, mono-[2-(meth)acryloyloxyethyl] maleate, and mono-[2-(meth)acryloyloxyethyl] phthalate.

These other copolymerizable unsaturated compounds may be used either individually or in combination of two or more.

The amount of the structural unit derived from such other copolymerizable unsaturated compounds in the polymer (I) is preferably 80 mol % or less, more preferably 60 mol % or less, and particularly preferably 40 mol % or less of the total amount of the structural units.

The polystyrene-reduced weight average molecular weight of the polymer (I) measured by gel permeation chromatography (hereinafter abbreviated as "Mw") is preferably 500–10,000, and preferably 1,000–5,000.

The molecular chains of the polymer (I) are crosslinkable by heating or exposure to light and, therefore, the polymer (I) is useful particularly for the antireflection film-forming composition described later. In addition, the polymer (I) can be used in paints, adhesives, insulating materials, formed articles, and the like either individually or in combination with other curable resins and curable rubbers.

Antireflection Film-Forming Composition

The antireflection film-forming composition of the present invention comprises (a) the polymer (I) and a solvent, (b) polymer (II) and a solvent, or (c) at least one polymer selected from the group consisting of the polymer (III), polymer (IV), and the polymer (V) and a solvent.

The polymers (II) to (V) and the solvent that make up the antireflection film-forming composition of the present invention will now be described.

Polymer (II)

As examples of the monovalent organic group represented by $R^4$ in the structural unit (4), the same groups as those previously given for the group $R^1$ in the structural unit (3) can be given. As examples of the monovalent atom or monovalent organic group represented by $R^5$, the same monovalent atoms or monovalent groups as those previously given for the group $R^2$ and $R^3$ in the structural unit (3) can be given.

A hydrogen atom, methyl group, and the like are particularly preferable for $R^4$ in the structural unit (4).

A hydrogen atom, methyl group, and the like are preferable as $R^5$ group.

The polymer (II) can be prepared by polymerizing an aromatic vinyl compound corresponding to the structural unit (4), optionally together with a copolymerizable unsaturated monomer by radical polymerization, anionic polymerization, cationic polymerization, or the like using an appropriate process such as a mass polymerization process or solution polymerization process.

The polymer (II) having the structural unit (4) in which the $R^4$ group is a hydrogen atom can be produced by hydrolyzing the acetoxy group of the polymer (II) having the structural unit (4) in which the $R^4$ group is an acetyl group by a conventional method. The polymer (II) having the structural unit (4) in which the $R^4$ group is an acetyl group can be produced by acetylating the hydroxyl group of the polymer (II) having the structural unit (4) in which the $R^4$ group is a hydrogen atom by a conventional method.

Preferable examples of the aromatic vinyl compound corresponding to the structural unit (4) include:
hydroxymethylstyrene compounds such as 2-hydroxymethylstyrene,
3-hydroxymethylstyrene, 4-hydroxymethylstyrene,
2-hydroxymethyl-α-methylstyrene,
3-hydroxymethyl-α-methylstyrene, and
4-hydroxymethyl-α-methylstyrene; methoxymethylstyrene compounds such as 2-methoxymethylstyrene,
3-methoxymethylstyrene, 4-methoxymethylstyrene,
2-methoxymethyl-α-methylstyrene,
3-methoxymethyl-α-methylstyrene, and
4-methoxymethyl-α-methylstyrene; styrene compounds such as
4-phenoxymethylstyrene, 4-phenoxymethyl-α-methylstyrene,
4-vinyloxymethylstyrene, 4-vinyloxymethyl-α-methylstyrene,
4-acetoxymethylstyrene, and 4-acetoxymethyl-α-methylstyrene;
hydroxymethyl vinylnaphthalene compounds such as
4-hydroxymethyl-1-vinylnaphthalene,
7-hydroxymethyl-1-vinylnaphthalene,
8-hydroxymethyl-1-vinylnaphthalene,
1-hydroxymethyl-2-vinylnaphthalene,
1-hydroxymethyl-3-vinylnaphthalene,
1-hydroxymethyl-4-vinylnaphthalene,
1-hydroxymethyl-5-vinylnaphthalene,
1-hydroxymethyl-6-vinylnaphthalene,
1-hydroxymethyl-7-vinylnaphthalene,
1-hydroxymethyl-8-vinylnaphthalene,
2-hydroxymethyl-3-vinylnaphthalene,
2-hydroxymethyl-4-vinylnaphthalene,
2-hydroxymethyl-5-vinylnaphthalene,
2-hydroxymethyl-6-vinylnaphthalene,
2-hydroxymethyl-7-vinylnaphthalene,
4-hydroxymethyl-1-isopropenylnaphthalene,
7-hydroxymethyl-1-isopropenylnaphthalene, and
8-hydroxymethyl-1-isopropenylnaphthalene;
methoxymethyl-1-vinylnaphthalene compounds such as
4-methoxymethyl-1-vinylnaphthalene,
7-methoxymethyl-1-vinylnaphthalene,
8-methoxymethyl-1-vinylnaphthalene,
4-methoxymethyl-1-isopropenylnaphthalene,
7-methoxymethyl-1-isopropenylnaphthalene, and
8-methoxymethyl-1-isopropenylnaphthalene; and other vinylnaphthalene compounds such as
4-phenoxymethyl-1-vinylnaphthalene,
4-vinyloxymethyl-1-vinylnaphthalene,
4-acetoxymethyl-1-vinylnaphthalene,
4-phenoxymethyl-1-isopropenylnaphthalene,
4-vinyloxymethyl-1-isopropenylnaphthalene,
4-acetoxymethyl-1-isopropenylnaphthalene.

Of these aromatic vinyl compounds, 4-hydroxymethylstyrene, 4-methoxymethylstyrene, 2-hydroxymethyl-6-vinylnaphthalene, and the like are particularly preferable.

These aromatic vinyl compounds may be used either individually or in combination of two or more.

The compounds previously given in the description relating to other copolymerizable unsaturated compounds in the polymer (I) can be given as examples of other copolymerizable unsaturated compounds in the polymer (II) used here.

Of such other copolymerizable unsaturated compounds, styrene is particularly preferable.

These other copolymerizable unsaturated compounds may be used either individually or in combination of two or more.

The amount of the structural unit derived from these other copolymerizable unsaturated compounds in the polymer (II) is preferably 80 mol % or less, more preferably 60 mol % or less, and particularly preferably 40 mol % or less of the total amount of the structural units.

Mw of the polymer (II) is suitably selected according to desired characteristics of the antireflection film, usually in the range of 500–10,000, and preferably 1,000–5,000.

Polymers (III) to (V)

The structural unit (3) of the polymer (I) is used as the structural unit (3) in the polymer (III) and polymer (IV). The structural unit (4) of the polymer (II) is used as the structural unit (4) in the polymer (IV) and polymer (V).

As examples of the monovalent atom or monovalent organic group represented by $R^6$ or $R^7$ in the structural unit (5), the same monovalent atoms or monovalent groups as those previously given for the groups $R^2$ and $R^3$ in the structural unit (3) can be given.

A hydrogen atom, methyl group, and the like are particularly preferable for $R^6$ and $R^7$ in the structural unit (5).

The polymer (III) can be prepared by polymerizing an acenaphthylene corresponding to the structural unit (3) and an aromatic vinyl compound corresponding to the structural unit (4), optionally together with another copolymerizable unsaturated monomer. The polymer (IV) can be prepared by polymerizing an acenaphthylene corresponding to the structural unit (3) and an acenaphthylene compound corresponding to the structural unit (5), optionally together with another copolymerizable unsaturated monomer. The polymer (V) can be prepared by polymerizing an aromatic vinyl compound corresponding to the structural unit (4) and an acenaphthylene corresponding to the structural unit (5), optionally together with another copolymerizable unsaturated monomer.

Radical polymerization, anionic polymerization, cationic polymerization, or the like using an appropriate process such as mass polymerization process, solution polymerization process, or the like can be used for manufacturing the polymers (III) to (V).

The polymer (III) having the structural unit (3) in which the $R^1$ group is a hydrogen atom or the structural unit (4) in which the $R^4$ group is a hydrogen atom, the polymer (IV) having the structural unit (3) in which the $R^1$ group is a hydrogen atom, and the polymer (V) having the structural unit (4) in which the $R^4$ group is a hydrogen atom can be respectively produced by hydrolyzing the acetoxymethyl group of the polymers (III), (IV), and (V) having the acetoxymethyl group by a conventional method. The polymer (III) having the structural unit (3) in which the $R^1$ group is an acetyl group or the structural unit (4) in which the $R^4$ group is an acetyl group, the polymer (IV) having the structural unit (3) in which the $R^1$ group is an acetyl group, and the polymer (V) having the structural unit (4) in which the $R^4$ group is an acetyl group can be respectively produced by acetylating the hydroxyl group of the polymers (III), (IV), and (V) having the hydroxyl group by a conventional method.

The compounds previously given in the description relating to the acenaphthylene corresponding to the structural unit (3) in the polymer (I) can be given as examples of the acenaphthylenes corresponding to the structural unit (3) in the polymers (III) and (IV) used here. Of these acenaphthylenes,
3-hydroxymethylacenaphthylene,
4-hydroxymethylacenaphthylene,
5-hydroxymethylacenaphthylene,
3-methoxymethylacenaphthylene,
4-methoxymethylacenaphthylene, and
5-methoxymethylacenaphthylene are particularly preferable.

These acenaphthylenes may be used either individually or in combinations of two or more.

The compounds previously given in the description relating to the aromatic vinyl compounds corresponding to the structural unit (4) in the polymer (II) can be given as examples of the aromatic vinyl compound corresponding to the structural unit (4) in the polymers (III) and (V) used here.

Of these aromatic vinyl compounds, 4-hydroxymethylstyrene, 4-methoxymethylstyrene, and the like are particularly preferable.

These aromatic vinyl compounds may be used either individually or in combination of two or more.

As examples of the preferable acenaphthylene corresponding to the structural unit (5) in the polymers (IV) and (V), acenaphthylene, 1-methylacenaphthylene, 1,2-dimethylacenaphthylene, 1-phenylacenaphthylene, 1,2-diphenylacenaphthylene, and 1-methyl-2-phenylacenaphthylene can be given.

Of these acenaphthylenes, acenaphthylene is particularly preferable.

These acenaphthylenes may be used either individually or in combinations of two or more.

The compounds previously given in the description relating to other copolymerizable unsaturated compounds in the polymer (I) can be given as other copolymerizable unsaturated compounds in the polymers (III), (IV), and (V) used here, for example.

These other copolymerizable unsaturated compounds may be used either individually or in combination of two or more.

In the polymer (III), the content of the structural unit (3) is preferably 5–80 mol %, more preferably 10–60 mol %, and particularly preferably 10–40 mol % of the total amount of the structural units, the content of the structural unit (4) is preferably 5–80 mol %, more preferably 5–60 mol %, and particularly preferably 5–40 mol %, and the content of the structural unit derived from other copolymerizable unsaturated compounds is 50 mol % or less, and more preferably 30 mol % or less.

In the polymer (IV), the content of the structural unit (3) is preferably 5–80 mol %, more preferably 10–60 mol %, and particularly preferably 10–40 mol % of the total amount of the structural units, the content of the structural unit (5) is preferably 5–95 mol %, more preferably 10–90 mol %, and particularly preferably 20–90 mol %, and the content of the structural unit derived from other copolymerizable unsaturated compounds is 50 mol % or less, and more preferably 30 mol % or less.

In the polymer (V), the content of the structural unit (4) is preferably 5–80 mol %, more preferably 10–60 mol %, and particularly preferably 15–60 mol % of the total amount of the structural units, the content of the structural unit (5) is preferably 5–95 mol %, more preferably 10–90 mol %, and particularly preferably 20–80 mol %, and the content of the structural unit derived from other copolymerizable unsaturated compounds is 50 mol % or less, and more preferably 30 mol % or less.

Mw of the polymers (III), (IV), and (V) is suitably selected according to desired characteristics of the antireflection film, usually in the range of 500–10,000, and preferably 500–5,000.

Solvent

Any solvent capable of dissolving the above-described polymers and later-described additives can be used for preparing the antireflection film-forming composition of the present invention without any specific limitation. Examples of the solvent that can be suitably selected include: ethylene glycol monoalkyl ethers such as ethylene glycol monomethyl ether, ethylene glycol monoethyl ether, ethylene glycol mono-n-propyl ether, and ethylene glycol mono-n-butyl ether; ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; diethylene glycol dialkyl ethers such as diethylene glycol dimethyl ether, diethylene glycol diethyl ether, diethylene glycol di-n-propyl ether, diethylene glycol di-n-butyl ether; triethylene glycol dialkyl ethers such as triethylene glycol dimethyl ether and triethylene glycol diethyl ether; propylene glycol monoalkyl ethers such as propylene glycol monomethyl ether, propylene glycol monoethyl ether, propylene glycol mono-n-propyl ether, and propylene glycol mono-n-butyl ether; propylene glycol dialkyl ethers such as propylene glycol dimethyl ether, propylene glycol diethyl ether, propylene glycol di-n-propyl ether, and propylene glycol di-n-butyl ether; propylene glycol monoalkyl ether acetates such as propylene glycol monomethyl ether acetate, propylene glycol monoethyl ether acetate, propylene glycol mono-n-propyl ether acetate, and propylene glycol mono-n-butyl ether acetate; lactic acid esters such as methyl lactate, ethyl lactate, n-propyl lactate, i-propyl lactate, n-butyl lactate, and i-butyl lactate; aliphatic carboxylic acid esters such as methyl formate, ethyl formate, n-propyl formate, i-propyl formate, n-butyl formate, i-butyl formate, n-amyl formate, i-amyl formate, methyl acetate, ethyl acetate, n-propyl acetate, i-propyl acetate, n-butyl acetate, i-butyl acetate, n-amyl acetate, i-amyl acetate, n-hexyl acetate, methyl propionate, ethyl propionate, n-propyl propionate, i-propyl propionate, n-butyl propionate, i-butyl propionate, methyl butyrate, ethyl butyrate, n-propyl butyrate, i-propyl butyrate, n-butyl butyrate, and i-butyl butyrate; other esters such as ethyl hydroxyacetate, ethyl 2-hydroxy-2-methylpropionate, methyl 3-methoxy-2-methylpropionate, methyl 2-hydroxy-3-methylbutyrate, ethyl methoxyacetate, ethyl ethoxyacetate, methyl 3-methoxypropionate, ethyl 3-ethoxypropionate, ethyl 3-methoxypropionate, 3-methoxypropyl acetate, 3-methoxybutyl acetate, 3-methyl-3-methoxybutyl acetate, 3-methyl-3-methoxybutyl propionate, 3-methyl-3-methoxybutyl butyrate, methyl acetoacetate, methyl pyruvate, and ethyl pyruvate; aromatic hydrocarbons such as toluene and xylene; ketones such as methyl ethyl ketone, methyl n-propyl ketone, methyl n-butyl ketone, 2-heptanone, 3-heptanone, 4-heptanone, and cyclohexanone; amides such as N-methylformamide, N,N-dimethylformamide, N-methylacetamide, N,N-dimethyl acetamide, and N-methylpyrrolidone; and lactones such as γ-butyrolactone.

Of these solvents, ethylene glycol monoethyl ether acetate, ethyl lactate, n-butyl acetate, ethyl 3-ethoxypropionate, methyl 3-methoxypropionate, 2-heptanone, cyclohexanone, and the like are preferable. These solvents may be used either individually or in combination of two or more. The solvent is used in an amount to make the solid content in the resulting composition usually 0.01–70 wt %, preferably 0.05–60 wt %, and more preferably 0.1–50 wt %.

Additives

Additives such as an acid generator, crosslinking agent, binder resin, radiation absorbent, and surfactant may be optionally added to the antireflection film-forming composition of the present invention to the extent not impairing the effect of the present invention. The addition of an acid generator and/or crosslinking agent is particularly preferable.

The acid generator is a component that generates an acid upon exposure to light or when heated.

The following compounds can be given as examples of the acid generator that generates an acid upon exposure to light (hereinafter referred to as "photoacid generator"): onium salt photoacid generators such as diphenyliodonium trifluoromethanesulfonate, diphenyliodonium nonafluoro-n-butanesulfonate, diphenyliodonium pyrenesulfonate, diphenyliodonium n-dodecylbenzenesulfonate, diphenyliodonium 10-camphorsulfonate, diphenyliodonium naphthalenesulfonate, diphenyliodonium hexafluoroantimonate, bis(4-t-butylphenyl)iodonium trifluoromethanesulfonate, bis(4-t-butylphenyl)iodonium nonafluoro-n-butanesulfonate, bis(4-t-butylphenyl)iodonium n-dodecylbenzenesulfonate, bis(4-t-butylphenyl)iodonium 10-camphorsulfonate, bis(4-t-butylphenyl)iodonium naphthalenesulfonate, bis(4-t-butylphenyl)iodonium hexafluoroantimonate, triphenylsulfonium trifluoromethanesulfonate, triphenylsulfonium nonafluoro-n-butanesulfonate, triphenylsulfonium n-dodecylbenzenesulfonate, triphenylsulfonium naphthalenesulfonate, triphenylsulfonium 10-camphorsulfonate, triphenylsulfonium hexafluoroantimonate, 4-hydroxyphenyl-phenyl-methylsulfonium p-toluenesulfonate, 4-hydroxyphenyl.benzyl.methylsulfonium p-toluenesulfonate, cyclohexyl.methyl.2-oxocyclohexylsulfonium trifluoromethanesulfonate, 2-oxocyclohexyldicyclohexylsulfonium trifluoromethanesulfonate, 2-oxocyclohexyldimethylsulfonium trifluoromethanesulfonate, 1-naphthyldimethylsulfonium trifluoromethanesulfonate, 1-naphthyldiethylsulfonium trifluoromethanesulfonate, 4-cyano-1-naphthyldimethylsulfonium trifluoromethanesulfonate, 4-cyano-1-naphthyldimethylsulfonium trifluoromethanesulfonate, 4-nitro-1-naphthyldimethylsulfonium trifluoromethanesulfonate, 4-nitro-1-naphthyldiethylsulfonium trifluoromethanesulfonate, 4-methyl-1-naphthyldimethylsulfonium trifluoromethanesulfonate, 4-methyl-1-naphthyldiethylsulfonium trifluoromethanesulfonate, 4-hydroxy-1-naphthyldimethylsulfonium trifluoromethanesulfonate, 4-hydroxy-1-naphthyldiethylsulfonium trifluoromethanesulfonate, 1-(4-hydroxynaphthalen-1-yl)tetrahydrothiophenium trifluoromethanesulfonate, 1-(4-methoxynaphthalen-1-yl)tetrahydrothiophenium trifluoromethanesulfonate, 1-(4-ethoxynaphthalen-1-yl)tetrahydrothiophenium trifluoromethanesulfonate, 1-(4-methoxymethoxynaphthalen-1-yl)tetrahydrothiophenium trifluoromethanesulfonate, 1-(4-ethoxymethoxynaphthalen-1-yl)tetrahydrothiophenium trifluoromethanesulfonate, 1-[4-(1-methoxyethoxy)naphthalen-1-yl]tetrahydrothiophenium trifluoromethanesulfonate, 1-[4-(2-methoxyethoxy)naphthalen-1-yl]tetrahydrothiophenium trifluoromethanesulfonate, 1-(4-methoxycarbonyloxynaphthalen-1-yl)tetrahydrothiophenium trifluoromethanesulfonate, 1-(4-ethoxycarbonyloxynaphthalen-1-yl)tetrahydrothiophenium trifluoromethanesulfonate, 1-(4-n-propoxycarbonyloxynaphthalen-1-yl)tetrahydrothiophenium trifluoromethanesulfonate, 1-(4-i-propoxycarbonyloxynaphthalen-1-yl)tetrahydrothiophenium trifluoromethanesulfonate, 1-(4-n-butoxycarbonyloxynaphthalen-1-yl)-tetrahydrothiophenium trifluoromethanesulfonate, 1-(4-t-butoxycarbonyloxynaphthalen-1-yl)-tetrahydrothiophenium trifluoromethanesulfonate, 1-[4-(2-tetrahydrofuranyloxy)naphthalen-1-yl]-tetrahydrothiophenium trifluoromethanesulfonate, 1-[4-(2-tetrahydropyranyloxy)naphthalen-1-yl]-tetrahydrothiophenium trifluoromethanesulfonate, 1-(4-benzyloxy)tetrahydrothiophenium trifluoromethanesulfonate, and 1-(naphthylacetomethyl)tetrahydrothiophenium trifluoromethanesulfonate; halogen-containing photoacid generators such as phenylbis(trichloromethyl)-s-triazine, 4-methoxyphenylbis(trichloromethyl)-s-triazine, and 1-naphthylbis(trichloromethyl)-s-triazine; diazoketone compound photoacid generators such as 1,2-naphthoquinonediazido-4-sulfonyl chloride, 1,2-naphthoquinonediazido-5-sulfonyl chloride, 1,2-naphthoquinonediazido-4-sulfonate or 1,2-naphthoquinonediazido-5-sulfonate of 2,3,4,4'-tetrahydroxybenzophenone; sulfone compound photoacid generators such as 4-trisphenacylsulfone, mesitylphenacylsulfone, and bis(phenylsulfonyl)methane; and sulfonate compound photoacid generators such as benzointosylate, pyrogallol tris (trifluoromethanesulfonate), nitrobenzyl-9,10-diethoxyanthracene-2-sulfonate, trifluoromethanesulfonylbicyclo[2,2,1]hept-5-ene-2,3-dicarb odiimide, N-hydroxysuccinimido trifluoromethanesulfonate, and 1,8-naphthalenedicarboxylic acid imide trifluoromethanesulfonate.

Of these photoacid generators, diphenyliodonium trifluoromethanesulfonate, diphenyliodonium nonafluoro-n-butanesulfonate, diphenyliodonium pyrenesulfonate, diphenyliodonium n-dodecylbenzenesulfonate, diphenyliodonium 10-camphorsulfonate, diphenyliodonium naphthalenesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium n-dodecylbenzenesulfonate, bis(4-t-butylphenyl)iodonium 10-camphorsulfonate, bis(4-t-butylphenyl)iodonium naphthalenesulfonate, and the like are preferable.

The photoacid generators may be used either individually or in combination of two or more.

As the acid generators generating an acid when heated (hereinafter referred to as "heat acid generator"), 2,4,4,6-tetrabromocyclohexadienone, benzointosylate, 2-nitrobenzyltosylate, alkyl sulfonates, and the like can be given.

These heat acid generators may be used either individually or in combination of two or more.

The photoacid generator and heat acid generator may be used in combination. The amount of acid generators to be added is usually 5,000 parts by weight or less, preferably 0.1–1,000 parts by weight, and particularly preferably 0.1–100 parts by weight for 100 parts by weight of the solid content of the antireflection film-forming composition. The addition of a photoacid generator and/or a heat acid generator to the antireflection film-forming composition of the present invention ensures the molecular chains in the polymers to effectively crosslink at a relatively low temperature, including a room temperature.

The crosslinking agent is a component effective for preventing intermixing between the resulting antireflection film and a resist coating produced thereon and also preventing cracks in the antireflection film.

Polynuclear phenolic compounds and various commercially available curing agents can be used as such a crosslinking agent.

As examples of the polynuclear phenolic compound, binuclear phenols such as 4,4'-biphenyldiol, 4,4'-methylenebisphenol, 4,4'-ethylidenebisphenol, and bisphenol A; trinuclear phenols such as 4,4',4''-methylidenetrisphenol, and 4,4'-[1-{4-(1-[4-hydroxyphenyl]-1-methylethyl)phenyl}-ethylidene]bisphenol; and polyphenols such as novolaks can be given.

Of these polynuclear phenolic compounds, 4,4'-[1-{4-(1-[4-hydroxyphenyl]-1-methylethyl)phenyl}-ethylidene] bisphenol, novolaks, and the like are preferable.

These polynuclear phenolic compounds may be used either individually or in combination of two or more.

As curing agents, diisocyanates such as 2,3-tolylene diisocyanate, 2,4-tolylene diisocyanate, 3,4-tolylene diisocyanate, 3,5-tolylene diisocyanate, 4,4'-diphenylmethane diisocyanate, hexamethylene diisocyanate, and 1,4-cyclohexane diisocyanate; commercially available products such as epoxy compounds, such as Epikoto 812, 815, 826, 828, 834, 836, 871, 1001, 1004, 1007, 1009, 1031 (manufactured by Japan Epoxy Resins Co., Ltd.); Araldite 6600, 6700, 6800, 502, 6071, 6084, 6097, 6099 (manufactured by Ciba Specialty Chemicals Inc.); DER331, 332, 333, 661, 644, 667 (manufactured by Dow Chemical Company); melamine-type curing agents such as Cymel 300, 301, 303, 350, 370, 771, 325, 327, 703, 712, 701, 272, 202, Mycoat 506, 508 (manufactured by Mitsui Cyanamid); benzoquanamine-type curing agents such as Cymel 1123, 1123-10, 1128, Mycoat 102, 105, 106, 130 (manufactured by Mitsui Cytec, Ltd.); and glycoluril-type curing agents such as Cymel 1170, 1172 (manufactured by Mitsui Cytec, Ltd.) and NIKALAC N-2702 (manufactured by Sanwa Chemical Co., Ltd.); and the like can be given.

Of these curing agents, melamine-type curing agents, glycoluril-type curing agents, and the like are preferable.

These curing agents may be used either individually or in combination of two or more.

In addition, the polynuclear phenolic compound and curing agent can be used in combination as crosslinking agent. The amount of crosslinking agents to be added is usually 5,000 parts by weight or less, and preferably 1,000 parts by weight or less, for 100 parts by weight of the solid content of the antireflection film-forming composition.

As the above binder resins, various thermoplastic resins and thermoset (or heat curable) resins can be used.

Given as examples of the thermoplastic resins are: α-olefin polymers such as polyethylene, polypropylene, poly-1-butene, poly-1-pentene, poly-1-hexene, poly-1-heptene, poly-1-octene, poly-1-decene, poly-1-dodecene, poly-1-tetradecene, poly-1-hexadecene, poly-1-octadecene, and polyvinylcycloalkane; non-conjugated diene polymers such as poly(1,4-pentadiene), poly(1,4-hexadiene), and poly(1,5-hexadiene); α,β-unsaturated aldehyde polymers; α,β-unsaturated ketone polymers such as poly(methyl vinyl ketone), poly(aromatic vinyl ketone) and poly(cyclic vinyl ketone); polymers of α,β-unsaturated carboxylic acids or their derivatives such as (meth) acrylic acid, α-chloroacrylic acid, (meth)acrylic acid salts, (meth)acrylic acid esters, (meth) acrylic acid halides, and the like; polymers of α,β-unsaturated carboxylic acid anhydrides such as poly (meth) acrylic acid anhydride and copolymers of maleic acid anhydride; polymers of unsaturated polybasic carboxylic acid esters such as methylene malonic acid diester and itaconic acid diester; polymers of diolefin carboxylic acid esters such as sorbic acid ester and muconic acid ester; polymers of α,β-unsaturated carboxylic acid thioesters such as (meth) acrylic acid thioester and α-chloroacrylic acid thioester; polymers of (meth)acrylonitrile or its derivatives such as (meth)acrylonitrile and α-chloroacrylonitrile; polymers of (meth)acrylamide or its derivatives such as (meth)acrylamide and N,N-dimethyl(meth)acrylamide; polymers of styryl metallic compounds; polymers of vinyloxy metallic compounds; polyimines; polyethers such as polyphenylene oxide, poly(1,3-dioxolane), polyoxirane, polytetrahydrofuran, and polytetrahydropyrane; polysulfides; polysulfonamides; polypeptides; polyamides such as Nylon 66 and Nylons 1 to 12; polyesters such as aliphatic polyester, aromatic polyester, alicyclic polyester, and polycarbonate; polyureas; polysulfones; polyazines; polyamines; polyaromatic ketones; polyimides; polybenzoimidazoles; polybenzoxazoles; polybenzothiazoles; polyaminotriazoles; polyoxadiazoles; polypyrazoles; polytetrazoles; polyquinoxalines; polytriazines; polybenzoxazinones; polyquinolines; and anthrazolines.

The heat curable resins are components becoming insoluble in solvents by curing with heat and preventing intermixing between the resulting antireflection film and a resist coating formed thereon. The resins can be preferably used as the binder resins.

As examples of such a heat-curable resin, heat-curable acrylic resins, phenol resins, urea resins, melamine resins, amino-type resins, aromatic hydrocarbon resins, epoxy resins, and alkyd resins can be given.

Of these heat curable resins, urea resins, melamine resins, aromatic hydrocarbon resins, and the like are preferable.

The above binder resins may be used either individually or in combination of two or more.

The amount of binder resin to be added is usually 20 parts by weight or less, and preferably 10 parts by weight or less, for 100 parts by weight of the polymers in the antireflection film-forming composition.

As the radiation absorbers, dyes such as oil soluble dyes, disperse dyes, basic dyes, methine-type dyes, pyrazole-type dyes, imidazole-type dyes, and hydroxyazo-type dyes; fluorescent brightening agents such as bixin derivatives, norbixin, stilbene, 4,4'-diaminostilbene derivatives, coumarin derivatives, and pyrazoline derivatives; UV absorbers such as hydroxyazo-type dyes, Tinuvin 234 (manufactured by Ciba Specialty Chemicals, Inc.), and Tinuvin 1130 (manufactured by Ciba Specialty Chemicals, Inc.); aromatic compounds such as anthracene derivatives and anthraquinone derivatives; and the like can be given.

These radiation absorbers may be used either individually or in combination of two or more.

The amount of radiation absorber to be added is usually 100 parts by weight or less, and preferably 50 parts by weight or less, for 100 parts by weight of the solid content of the antireflection film-forming composition.

The surfactants are components exhibiting the effects of improving applicability, striation, wettability, and developability.

As the surfactants, nonionic surfactants such as polyoxyethylene lauryl ether, polyoxyethylene stearyl ether, polyoxyethylene oleyl ether, polyoxyethylene n-octyl phenyl ether, polyoxyethylene n-nonyl phenyl ether, polyethylene glycol dilaurate, and polyethylene glycol distearate; commercially available products such as KP341 (manufactured by Shin-Etsu Chemical Co., Ltd.), Polyflow No. 75, No. 95 (manufactured by Kyoeisha Chemical Co., Ltd.), FFTOP EF101, EF204, EF303, EF352 (manufactured by JEMCO, Inc.), MEGAFACE F171, F172, F173 (manufactured by Dainippon Ink and Chemicals, Inc.), Fluorad FC430, FC431, FC135, FC93 (manufactured by Sumitomo 3M Ltd.), Asahi Guard AG710, Surflon S382, SC101, SC102, SC103, SC104, SC105, SC106 (manufactured by Asahi Glass Co., Ltd.), and the like can be given.

The surfactants may be used either individually or in combination of two or more.

The amount of surfactant to be added is usually 15 parts by weight or less, and preferably 10 parts by weight or less, for 100 parts by weight of the solid content of the antireflection film-forming composition.

As other additives, storage stabilizers, anti-foaming agents, adhesion adjuvants, and the like can be given.

Process for Forming Antireflection Film

The process for forming an antireflection film from the antireflection film-forming composition (hereinafter referred to as "composition") of the present invention comprises, for example, 1) a step of forming an antireflection film on a substrate by applying the composition onto a substrate and curing the coating, 2) a step of forming a resist film by applying a resist composition solution onto the antireflection film and prebaking the applied coating, 3) a step of exposing selected areas of the resist coating to radiation through a photomask, 4) a step of developing the exposed resist coating, and 5) a step of etching the antireflection film.

A silicon wafer or a wafer coated with aluminum, for example, can be used as the substrate in step 1). The composition is coated by an appropriate method such as rotation application, cast coating, and roll application.

The coating film is cured by radiation and/or heat. The type of radiation used for exposure is appropriately selected according to the type of photoacid generator from among visible radiation, ultraviolet radiation, deep ultraviolet rays, X-rays, electronbeams, γ-rays, molecularbeams, ion beams, and the like. When the composition containing a photoacid generator is exposed to light, the coating film can be effectively cured at a room temperature. Usually, the heating temperature is about 90–350° C., and preferably about 200–300° C. However, when the composition contains a photoacid generator, the coating film can be effectively cured at about 90–150° C., for example.

The thickness of the antireflection film formed in step 1) is usually 0.1–5 μm.

Next, in step 2), the resist film having a specific thickness is formed by applying the resist composition solution on the antireflection film so that the resulting resist film may have a prescribed thickness and by prebaking the resulting coating to volatilize the solvent. In this instance, the prebaking temperature is appropriately adjusted according to the type of resist composition in the range usually of 30–200° C., and preferably of 50–150° C.

As the resist composition, a chemically amplified positive tone or negative tone resist composition containing a photoacid generator, a positive tone resist composition comprising an alkali-soluble resin and a quinone diazido sensitizer, a negative tone resist composition comprising an alkali-soluble resin and a crosslinking agent, and the like can be given.

The resist composition solution used for forming a resist film on the antireflection film has a solid component content usually of about 5–50 wt % and is used for resist film formation after filtering through a filter with a pore diameter of about 0.2 μm. A commercially available resist composition solution can be used as is in this step.

Radiation used for exposure in step 3) is appropriately selected according to the type of photoacid generator used in the resist composition from among visible rays, ultraviolet rays, deep ultraviolet rays, X-rays, electron beams, γ-rays, molecular beams, ion beams, and the like. Of these radiations, deep ultraviolet rays, particularly a KrF excimer laser (wavelength: 248 nm), ArF excimer laser (wavelength: 193 nm), $F_2$ excimer laser (wavelength: 157 nm), $Kr_2$ excimer laser (wavelength: 147 nm), ArKr excimer laser (wavelength: 134 nm), and extreme ultraviolet rays (wavelength: 13 nm) are preferable.

Next, in step 4), the resist film after exposure is developed, washed, and dried to form a target resist pattern. In this step, postbaking may be carried out after exposure and before development to improve resolution, pattern profile, developability, and the like.

The developer used in this step is appropriately selected from the type of resist composition used. As examples of the developer used for a chemically amplified positive tone resist composition or a positive tone resist composition containing an alkali-soluble resin, alkaline aqueous solutions prepared by dissolving alkaline compounds such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, choline, 1,8-diazabicyclo-[5.4.0]-7-undecene, and 1,5-diazabicyclo-[4.3.0]-5-nonene can given. An appropriate amount of a water-soluble organic solvent such as alcohols including methanol and ethanol or a surfactant can be added to these alkaline aqueous solutions.

Next, in step 5), the antireflection film is etched by dry etching using the obtained resist pattern as a mask and a gas plasma such as oxygen plasma to obtain a desired resist pattern for substrate processing.

EXAMPLES

The present invention is described below in more detail by examples. However, these examples should not be construed as limiting the present invention. In the examples, part(s) and % refer to part(s) by weight and wt % unless otherwise indicated.

Example 1

Synthesis of Acenaphthylene Derivative

Step 1

150 g of tin chloride was added dropwise to a solution of dichloromethyl methyl ether (70 g) in dichloroethane (300 g) while stirring at −5° C. under a dry atmosphere. Then, a solution of acenaphthene (77 g) in dichloroethane (300 g) was added. After stirring for two hours at room temperature, an aqueous solution of 5% calcium chloride was slowly added to the reaction solution. The organic phase was washed until the water phase becomes neutral and then removed. The solvent was evaporated to obtain 90.5 g of a pale yellow solid compound.

$^1$H-NMR spectrum (solvent: deuterium chloroform, hereinafter the same) and IR spectrum were measured to identify the compound to be formyl acenaphthene. The measurement results were as follows.

σ (unit ppm): 3.4 ($CH_2$ group)
7.3–8.8, 10.5 (CHO group)
IR (unit $cm^{-1}$): 1677 (C=O group)

Step 2

Formyl acenaphthene (73 g) obtained in Step 1 was dissolved in a mixed solvent of tetrahydrofuran and ethanol (tetrahydrofuran: 550 g, ethanol: 110 g). Sodium borohydride (7.6 g) was added to the solution and the mixture was stirred for two hours at room temperature. The reaction solution was concentrated and water was added to the residue to collect a deposited compound by filtration. The filtrate was dried under reduced pressure to obtain 71 g of white solid.

$^1$H-NMR spectrum (δ) and IR spectrum were measured to identify the compound to be hydroxymethylacenaphthene. The measurement results were as follows.

σ (unit ppm): 3.3 ($CH_2$ group)
4.8–4.9 ($CH_2$—O group)
5.2–5.3 (OH group)
7.2–7.8 (hydrogen atom of aromatic ring)
IR (unit $cm^{-1}$): 3372, 3297 (OH groups)

Step 3

Hydroxymethylacenaphthene (55 g) obtained in Step 2 was dissolved in dioxane (1,200 g). Acetyl chloride (26 g) and triethylamine (36 g) were added to the solution in this order while maintaining the temperature to 50° C. or less. The mixture was stirred for three hours at 90° C. Insoluble components were separated by filtration. The organic phase was concentrated and the solvent was replaced with toluene. The toluene solution was washed until the water phase becomes neutral. The solvent was evaporated to obtain 65 g of a yellow solid compound.

$^1$H-NMR spectrum (δ) and IR spectrum were measured to identify the compound to be acetoxymethylacenaphthene. The measurement results were as follows.

σ (unit ppm): 2.1 ($CH_3$ group)
3.3–3.4 ($CH_2$ group)
5.5 ($CH_2$—O group)
7.2–7.5 (hydrogen atom of aromatic ring)
IR (unit $cm^{-1}$): 1725 (C=O group)

Step 4

The acetoxymethylacenaphthene (45 g) obtained in Step 3 was dissolved in dioxane (450 g). After the addition of dichlorodicyanobenzoquinone (60 g), the mixture was stirred for seven hours at 95° C. The reaction mixture was filtered and the solvent was evaporated from the filtrate to obtain 54 g of acetoxymethylacenaphthylene as a brown solid.

Step 5

Acetoxymethylacenaphthylene (44 g) was dissolved in methanol (300 g). After the addition of 10% NaOH aqueous solution (110 g) dropwise, the mixture was stirred for two hours at 60° C. Methanol was evaporated from the reaction solution to replace the solvent with methyl ethyl ketone (350 g). The methyl ethyl ketone solution was washed until the water phase becomes neutral. The solvent was evaporated to obtain a yellow solid compound. The yellow solid compound was purified by recrystallization to obtain 10 g of a compound.

$^1$H-NMR spectrum (δ) and IR spectrum were measured to identify the compound to be hydroxymethylacenaphthylene. The measurement results were as follows.

σ (unit ppm): 5.1 ($CH_2$—O group)
5.4 (OH group)
7.2 (HC=CH group)
7.6–8.2 (hydrogen atom of aromatic ring)
IR (unit $cm^{-1}$): 3423 (OH group)

Synthesis Example 1

(Synthesis of 2-hydroxymethyl-6-vinylnaphthalene)

Methyl 6-bromo-2-naphthalene carboxylate (98 g) was dissolved in dimethoxyethane (2 1) and tetrakis(triphenylphosphine)palladium (44 g) was added in nitrogen atmosphere. The mixture was stirred for 30 minutes at room temperature. Potassium carbonate (52 g), water (1 1) and 2,4,6-trivinylcyclotriboroxane-pyridine complex (91 g) were added and the mixture was stirred for 24 hours while refluxing with heating. There action mixture was cooled to room temperature and treated with activated alumina to obtain methyl 2-vinyl-6-naphthalene carboxylate (77 g).

The methyl 2-vinyl-6-naphthalene carboxylate (30 g) was dissolved in tetrahydrofuran and 1 M diisobutylaluminum hydride (DIBAL-H) solution (400 ml) was added at −78° C. After confirming completion of the reaction with thin layer chromatography, the reaction mixture was treated with methanol and water, and extracted with ethyl acetate.

The organic layer was washed with brine, dried over anhydrous sodium sulfate, filtered, and concentrated.

The residue was purified by silica gel column chromatography to obtain a compound (18.5 g).

$^1$H-NMR spectrum (δ) shown below identified that the compound was 2-hydroxymethyl-6-vinylnaphthalene.

σ (unit ppm): 4.9 (CH$_2$—O group)

5.3, 5.9, 6.9 (vinyl group), 7.6–7.8 (hydrogen atom on aromatic ring)

In the following Preparation Example 1 and Examples 2–3, Mw of the obtained polymers was measured by gel permeation chromatography (detector: differential refractometer) using GPC columns (manufactured by Tosoh Corp., G2000H$^{XL}$×2, G3000H$^{XL}$×1) under the following conditions. Flow rate: 1.0 ml/minute, eluate: tetrahydrofuran, column temperature: 40° C., reference material: monodispersed polystyrene.

Performance of antireflection film-forming compositions was evaluated as follows.

<Optical Characteristics>

The antireflection film-forming composition was spin-coated on a silicon wafer with a diameter of eight inches and heated for 120 seconds on a hot plate at 345° C. to obtain an antireflection film with a thickness of 1 μn. Refractive index (n value) and absorbance (k value) of the antireflection film were measured at a wavelength of 248 nm using a spectroscopic Ellipsometer UV-1280E (manufactured by KLA-TENCOR Corp.). The n value and k value were also measured at a wavelength of 193 nm using a spectroscopic Ellipsometer MOSS-ESVG DEEP UV (manufactured by SOPRA Inc.).

<Formation of Positive Type Resist Pattern for KrF>

The antireflection film-forming composition was spin coated on a silicon wafer with a diameter of 8 inch and heated for 120 seconds on a hot plate at 345° C. to obtain an antireflection film with a thickness of 0.6 μm. A resist composition solution for KrF (KRFM 20G, manufactured by JSR Corporation) was spin coated onto the antireflection film and prebaked for 60 seconds on a hot plate at 140° C. to obtain a resist film with a thickness of 0.61 μm. The resist film was exposed to a KrF excimer laser using a stepper NSR2205 EX12B (wavelength: 248 nm, manufactured by Nikon Corp.) through a mask at an optimal dose for producing a 1:1 line-and-space pattern with a line width of 0.22 μm. After postbaking on a hot plate at 140° C. for 90 seconds, the resist film was developed using a 2.38 wt % tetramethylammonium hydroxide aqueous solution at 23° C. for 30 minute, washed with water, and dried to form a positive-tone resist pattern.

<Formation of Positive Type Resist Pattern for ArF>

The antireflection film-forming composition was spin coated on a silicon wafer with a diameter of eight inches and baked for 120 seconds on a hot plate at 345° C. to obtain an antireflection film with a thickness of 0.6 μm. A resist composition solution for ArF obtained in Reference Example 1 described later was spin coated onto the antireflection film and prebaked for 90 seconds on a hot plate at 130° C. to obtain a resist film with a thickness of 0.5 μm. The film was exposed to ArF excimer laser through a mask pattern using an ArF excimer laser exposure apparatus (manufactured by Integrated Solutions Inc., lens numerical aperture: 0.60, wavelength: 193 nm) at an optimum dose. After postbaking on a hot plate at 130° C. for 90 seconds, the resist film was developed using a 2.38 wt % tetramethylammonium hydroxide aqueous solution at 25° C. for one second, washed with water, and dried to form a positive-tone resist pattern.

<Standing Wave Prevention Effect>

Antireflection film formation, resist film formation, exposure, and development were carried out in the above-described manner to observe and evaluate an effect of standing wave on a resist film using a scanning type electron microscope.

<Intermixing Prevention Effect>

The antireflection film formed according to the above-described procedure was dipped in propyl glycol monomethyl ether acetate for one minute at room temperature. The film thickness was measured before and after dipping using a spectroscopic ellipsometer UV-1280E (manufactured by KLA-Tencor Corp.). The film of which the thickness did not change after dipping was rated as "O" and the film with a thickness change was rated as "X".

Preparation Example 1

Preparation of Resist Composition Solution for ArF

A separable flask equipped with a reflux condenser was charged with 8-methyl-8-t-butoxycarbonylmethoxycarbonyl-tetracyclo[4.4.0.1$^{2,5}$.1$^{7,10}$]dodec-3-ene (29 parts), 8-methyl-8-hydroxytetracyclo[4.4.0.1$^{2,5}$.1$^{7,10}$]dodec-3-ene (10 parts), maleic anhydride (18 parts), 2,5-dimethyl-2,5-hexanedioldiacrylate (4 parts), t-dodecylmercaptan (1 part), azobisisobutylonitrile (4 parts), and 1,2-diethoxyethane (6 parts) in a nitrogen stream. A polymerization reaction was carried out at 70° C. for 6 hours. After the polymerization, the reaction mixture was poured into a large amount of a 1:1 (by weight) mixed solvent of n-hexane/i-propyl alcohol to cause the resin to coagulate. The coagulated resin was washed with the solvent several times and dried under vacuum to obtain a resin containing the structural units of the following formula (a), (b), or (c) respectively in the amount of 64 mol %, 18 mol %, and 18 mol %, and having Mw of 27,000 at a yield of 60 wt %.

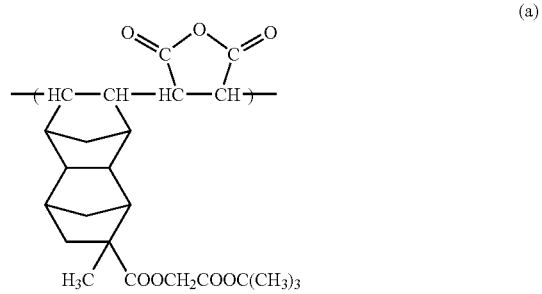

(a)

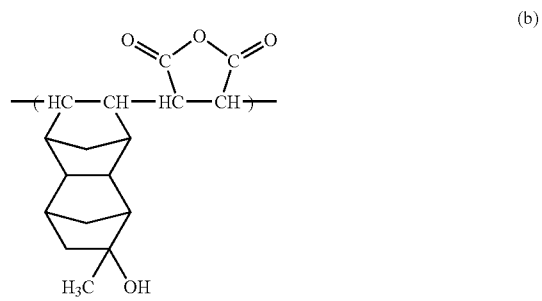

(b)

-continued

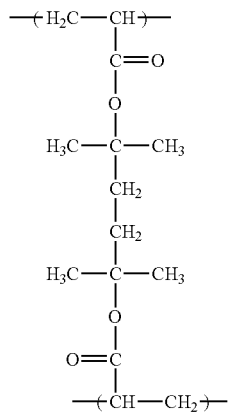

(c)

A resist composition solution for ArF was prepared by dissolving the resulting resin (80 parts), 1-(4-methoxy naphthalen-1-yl)tetrahydrothiophenium nonafluoro-n-butanesulfonate (1.5 parts), tri-n-octylamine (0.04 part) in propylene glycol monomethyl ether acetate (533 parts).

Example 2

Synthesis of Polymers (III)

A separable flask equipped with a thermometer was charged with acenaphthylene (8 parts), 5-hydroxymethylacenaphthylene (4 parts), n-butyl acetate (50 parts), and azobisisobutyronitrile (4 parts) in a nitrogen atmosphere. The mixture polymerized at 80° C. for seven hours while stirring. The reaction mixture was diluted with n-butyl acetate (100 parts) and the organic layer was washed with a large amount of a mixed solvent of water and methanol (weight ratio 1:2). The solvent was evaporated to obtain a Polymer (III) with an Mw of 1,000.

Example 3

Synthesis of Polymer (IV)

A separable flask equipped with a thermometer was charged with acenaphthylene (6 parts), 4-hydroxymethyl styrene (5 parts), n-butyl acetate (44 parts), and azobisisobutyronitrile (48 parts) in a nitrogen atmosphere. The mixture polymerized at 75° C. for seven hours while stirring. The reaction mixture was diluted with n-butyl acetate (100 parts) and the organic layer was washed with a large amount of a mixed solvent of water and methanol (weight ratio 1:2). The solvent was evaporated to obtain a Polymer (IV) with an Mw of 1,200.

Example 4

Synthesis of Polymer (V)

A separable flask equipped with a thermometer was charged with acenaphthylene (6 parts), 2-hydroxymethyl-6-vinylnaphthalene (5 parts), 2-heptanone (48 parts), and azobisisobutyronitrile (4 parts) in a nitrogen atmosphere. The mixture was polymerized at 75° C. for seven hours while stirring. The reaction mixture was diluted with 2-heptanone (100 parts) and the organic layer was washed with a large amount of a mixed solvent of water and methanol (weight ratio 1:2). The solvent was evaporated to obtain Polymer (V) with an Mw of 1,200.

Example 5

(Evaluation of Antireflection Film-Forming Composition)

The Polymer (III) obtained in Example 2 (10 parts), bis(4-t-butylphenyl)iodonium 10-camphorsulfonate (0.5 part), and 4,4'-[1-{4-(1-[4-hydroxyphenyl]-1-methylethyl)phenyl}-ethylidene]bisphenol (0.5 part) were dissolved in ethyl lactate (89 parts). The solution was filtered using a membrane filter with a pore diameter of 0.1 µm to prepare an antireflection film-forming composition. Properties of the composition were evaluated. The evaluation results are shown in Table 1.

Example 6

(Evaluation of Antireflection Film-Forming Composition)

The Polymer (III) obtained in Example 2 (10 parts), bis(4-t-butylphenyl)iodonium nonafluoro-n-butanesulfonate (0.5 part), and 4,4'-[1-{4-(1-[4-hydroxyphenyl]-1-methylethyl)phenyl}ethylidene]bisphenol (0.5 part) were dissolved in ethyl lactate (89 parts). The solution was filtered using a membrane filter with a pore diameter of 0.1 µm to prepare an antireflection film-forming composition. Properties of the composition were evaluated. The evaluation results are shown in Table 1.

Example 7

(Evaluation of Antireflection Film-Forming Composition)

An antireflection film-forming composition was obtained in the same manner as in Example 5, except for using 10 parts of Polymer (IV) obtained in Example 3 instead of 10 parts of Polymer (III) obtained in Example 2. Properties of the composition were evaluated. The evaluation results are shown in Table 1.

Example 8

(Evaluation of Antireflection Film-forming Composition)

An antireflection film-forming composition was obtained in the same manner as in Example 6, except for using 10 parts of Polymer (IV) obtained in Example 3 instead of 10 parts of Polymer (III) obtained in Example 2. Properties of the composition were evaluated. The evaluation results are shown in Table 1.

Example 9

(Evaluation of Antireflection Film-Forming Composition)

An antireflection film-forming composition was obtained in the same manner as in Example 6, except for using 10 parts of Polymer (V) obtained in Example 4 instead of 10 parts of Polymer (III) obtained in Example 2. Properties of the composition were evaluated. The evaluation results are shown in Table 1.

Comparative Example 1

A positive tone resist pattern for KrF and a positive tone resist pattern for ArF were formed without using an antireflection film-forming composition to evaluate the performance. The evaluation results are shown in Table 1.

TABLE 1

| | Optical characteristics Wavelength (nm) | | | | Standing wave prevention effect | Inter-mixing prevention effect |
|---|---|---|---|---|---|---|
| | 248 | | 193 | | | |
| | n-Value | k-Value | n-Value | k-Value | | |
| Example 5 | 2.2 | 0.4 | 1.4 | 0.4 | Yes | ○ |
| Example 6 | 2.2 | 0.4 | 1.4 | 0.4 | Yes | ○ |
| Example 7 | 2.0 | 0.3 | 1.5 | 0.6 | Yes | ○ |
| Example 8 | 2.0 | 0.3 | 1.5 | 0.6 | Yes | ○ |
| Example 9 | 2.2 | 0.4 | 1.4 | 0.4 | Yes | ○ |
| Comparative Example 1 | — | — | — | — | None | X |

Acetoxymethylacenaphthylene (1) and hydroxymethylacenaphthylene (2) of the present invention are particularly suitable for use as raw materials or intermediates for manufacturing Polymer (I).

The Polymer (I) of the present invention is particularly suitable for use as a polymer component for the antireflection film-forming composition of the present invention.

The antireflection film formed from the antireflection film-forming composition of the present invention exhibits a high antireflection effect and does not cause intermixing with a resist film. Therefore, the antireflection film can form an excellent resist pattern with superior sensitivity, pattern profile, and the like in cooperation with various positive-tone or negative-tone resist compositions. Therefore, the antireflection film-forming composition of the present invention can greatly contribute particularly to the manufacture of high integrated circuits.

The invention claimed is:

1. Acetoxymethylacenaphthylene of the following formula (1)

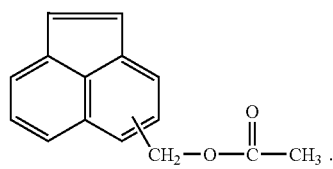

(1)

2. Hydroxymethylacenaphthylene of the following formula (2)

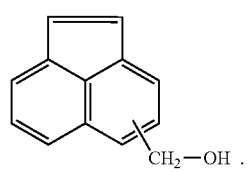

(2)

3. A polymer containing a structural unit of the following formula (3),

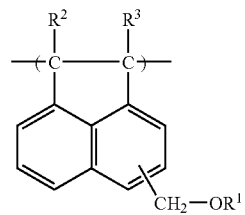

(3)

wherein $R^1$ is a hydrogen atom and $R^2$ and $R^3$ individually represent a monovalent atom or a monovalent organic group, the polymer having a polystyrene-reduced weight average molecular weight determined by gel permeation chromatography (GPC) in the range of 500 to 10,000.

4. An antireflection film-forming composition comprising the polymer of claim 3 and a solvent.

5. An antireflection film-forming composition comprising, a polymer having a structural unit of the following formula (4)

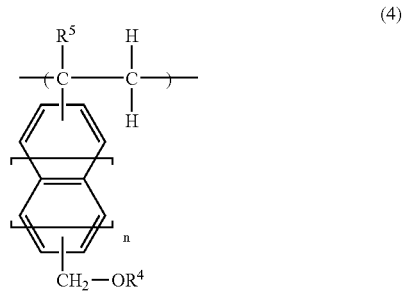

(4)

wherein $R^4$ is a monovalent organic group selected from the group consisting of a phenyl group, an alkyl group, an alkenyl group, an acyl group, and a group in which one or more hydrogen atoms of a phenyl group, an alkyl group, an alkenyl group, or an acyl group are replaced by one or more of the same or different substituents selected from the group consisting of a halogen atom, a hydroxyl group, a mercapto group, a nitro group and a sulfonic acid group, $R^5$ is a monovalent atom or a monovalent organic group, and n is 1, and a solvent.

6. An antireflection film-forming composition comprising, at least one polymer selected from the group consisting of: a polymer having a structural unit of the following formula (3)

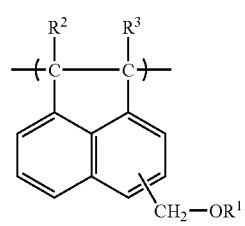

(3)

wherein $R^1$ is a hydrogen atom and $R^2$ and $R^3$ individually represent a monovalent atom or a monovalent organic group and a structural unit of the following formula (4)

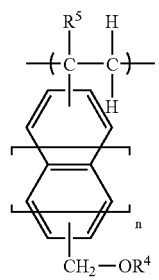 (4)

wherein $R^4$ is a hydrogen atom or a monovalent organic group, $R^5$ is a monovalent atom or a monovalent organic group, and n is 0 or 1; a polymer having a structural unit of the formula (3) and a structural unit of the following formula (5)

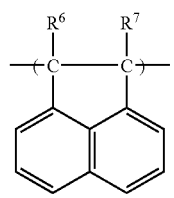 (5)

wherein $R^6$ and $R^7$ individually represent a monovalent atom or a monovalent organic group; and a polymer having a structural unit of the formula (4) and a structural unit of the formula (5); and
a solvent.

7. The antireflection film-forming composition according to claim 4, further comprising an acid generator.

8. The antireflection film-forming composition according to claim 5, further comprising an acid generator.

9. The antireflection film-forming composition according to claim 6, further comprising an acid generator.

10. An antireflection film-forming composition comprising:
a polymer having a structural unit of the following formula (4);

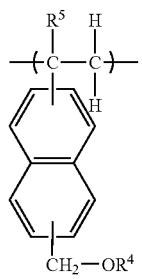

wherein $R^4$ is a hydrogen atom or a monovalent organic group and $R^5$ is a monovalent atom or a monovalent organic group; and
a solvent.

11. The antireflection film-forming composition according to claim 10, further comprising an acid generator.

12. An antireflection film-forming composition comprising,
a polymer having a structural unit of the following formula (4)

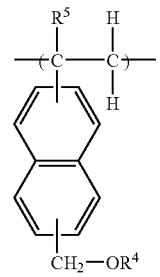

wherein $R^4$ is a monovalent organic group selected from the group consisting of a phenyl group, an alkenyl group, an acyl group, and a group in which one or more hydrogen atoms of a phenyl group, an alkyl group, an alkenyl group, or an acyl group are replaced by one or more of the same or different substituents selected from the group consisting of a halogen atom, a hydroxyl group, a mercapto group, a nitro group and a sulfonic acid group, $R^5$ is a monovalent organic group, and
a solvent.

13. The antireflection film-forming composition according to claim 12, further comprising an acid generator.

14. An antireflection film-forming composition comprising,
a polymer having a structural unit of the following formula (4)

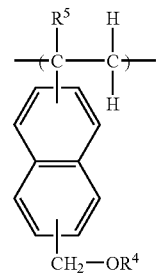

wherein $R^4$ is a monovalent organic group selected from the group consisting of an alkenyl group and a group in which one or more hydrogen atoms of a phenyl group, an alkyl group, an alkenyl group, or an acyl group are replaced by one or more of the same or different substituents selected from the group consisting of a halogen atom, a hydroxy group, a mercapto group, a nitro group and a sulfonic acid group, $R^5$ is a monovalent atom or a monovalent organic group, and
a solvent.

15. The antireflection film-forming composition according to claim 14, further comprising an acid generator.

* * * * *